United States Patent
Kim et al.

(10) Patent No.: US 10,952,956 B2
(45) Date of Patent: Mar. 23, 2021

(54) ANTIOXIDANT COMPOSITION FOR SKIN

(71) Applicant: AMOREPACIFIC CORPORATION, Seoul (KR)

(72) Inventors: Hyeon Chung Kim, Yongin-si (KR); Min Jeong Song, Yongin-si (KR); Eun Jung Lee, Yongin-si (KR); Nok Hyun Park, Yongin-si (KR); Ji Hyun Kim, Yongin-si (KR); Ji Yeong Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/308,746

(22) PCT Filed: Jun. 26, 2017

(86) PCT No.: PCT/KR2017/006691
§ 371 (c)(1),
(2) Date: Dec. 10, 2018

(87) PCT Pub. No.: WO2018/004212
PCT Pub. Date: Jan. 4, 2018

(65) Prior Publication Data
US 2019/0142735 A1  May 16, 2019

(30) Foreign Application Priority Data
Jun. 27, 2016 (KR) .......................... 10-2016-0080431

(51) Int. Cl.
*A61K 8/9728*     (2017.01)
*A61Q 19/00*      (2006.01)
*A61K 8/99*       (2017.01)
*A61K 8/02*       (2006.01)
*A61K 8/365*      (2006.01)
*A61K 8/66*       (2006.01)
*A61K 8/67*       (2006.01)
*A61Q 19/08*      (2006.01)

(52) U.S. Cl.
CPC .............. *A61K 8/9728* (2017.08); *A61K 8/02* (2013.01); *A61K 8/365* (2013.01); *A61K 8/66* (2013.01); *A61K 8/675* (2013.01); *A61K 8/99* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | |
|---|---|---|
| 2005/0085454 A1 | 4/2005 | Ghosal |
| 2008/0057088 A1 | 3/2008 | Blass et al. |
| 2009/0215122 A1* | 8/2009 | Yodoi .................. C12N 9/0036 435/71.1 |
| 2011/0144142 A1 | 6/2011 | Hu et al. |
| 2014/0127257 A1 | 5/2014 | Schiemann et al. |
| 2015/0250700 A1 | 9/2015 | Kim et al. |

FOREIGN PATENT DOCUMENTS

| | | | |
|---|---|---|---|
| CN | 104523555 A | 4/2015 | |
| CN | 104721129 A | 6/2015 | |
| EP | 2236127 A1 | 10/2010 | |
| JP | 2015-536979 A | 12/2015 | |
| KR | 10-2011-0076055 A | 7/2011 | |
| KR | 10-2012-0102111 A | 9/2012 | |
| KR | 10-2014-0060928 A | 5/2014 | |
| KR | 10-2015-0050234 A | 5/2015 | |
| KR | 10-2015-0050236 A | 5/2015 | |
| KR | 10-2015-0087146 A | 7/2015 | |
| KR | 10-2015-0144026 A | 12/2015 | |
| KR | 10-2016-0016382 A | 2/2016 | |
| WO | WO-2013000717 A2 * | 1/2013 | ........... A61K 36/064 |
| WO | 2014062607 A1 | 4/2014 | |
| WO | 2015030702 A2 | 3/2015 | |

OTHER PUBLICATIONS

Son et al. 2007 (Alpha-Ketoglutarate Stimulates Procollagen Production in Cultured Human Dermal Fibroblasts, and Decreases UVB-Induced Wrinkle Formation Following Topical Application on the Dorsal Skin of Hairless Mice; Biol. Pharm. Bull 30(8): 1395-1399) (Year: 2007).*
Draelos et al. 2006 (The effect of 2% niacinamide on facial sebum production; Journal of Cosmetic and Laser Therapy; 8:96-101). (Year: 2006).*
International Search Report for Corresponding International Application No. PCT/KR2017/006691 (2 Pages) (dated Sep. 20, 2017).

* cited by examiner

*Primary Examiner* — Mary Maille Lyons
(74) *Attorney, Agent, or Firm* — Lucas & Mercanti, LLP

(57) ABSTRACT

The present invention relates to an antioxidant composition for the skin. More specifically, it relates to an antioxidant composition for the skin having: *Saccharomyces* ferment; and α-ketoglutaric acid or niacinamide alone or a mixture thereof. The antioxidant composition for the skin according to the present invention has not only an excellent antioxidant effect but also a high long lasting effect. Therefore, it provides an enhanced antioxidant effect when applied to the skin and it enables manufacture of various products such as cosmetics and medicines because it is not harmful to the human body.

4 Claims, No Drawings

ANTIOXIDANT COMPOSITION FOR SKIN

CROSS-REFERENCE(S) TO RELATED APPLICATION

This application is a 371 of PCT/KR2017/006691, filed Jun. 26, 2017 which claims the benefit of Korean Patent Application No. 10-2016-0080431, filed Jun. 27, 2016, the contents of each of which are incorporated herein by reference.

FIELD OF THE INVENTION

Technical Field

The present invention relates to an antioxidant composition for the skin having enhanced antioxidant effect.

Background Art

The skin is the primary barrier of the human body, which functions to protect the organs of the body from external environmental stimuli such as changes in temperature and humidity, UV rays and pollutants.

The human skin undergoes changes with aging due to a variety of intrinsic and extrinsic factors. Specifically, with respect to the intrinsic factors, the secretion of various hormones that regulate metabolisms decreases, and the function of immune cells and the activity of cells decrease, so that the biosynthesis of immune proteins required for the body and constituent proteins of the body decreases. With respect to the extrinsic factors, as exposure to UV rays becomes excess, and free radicals and reactive oxygen species increase, various changes in the skin occur, including reduced thickness, increased wrinkles, reduced skin elasticity, dark skin color, frequent occurrence of skin troubles, increased age spots, freckles and dark spots.

Recently, the increase of reactive oxygen species (ROS) caused by stress due to various harmful environments and sunlight accelerates the decomposition and denaturation of substances constituting the skin. As a result, the skin substrate is destroyed and thinned to cause various diseases, for example, various symptoms of aging of the skin, as well as promoting aging of the living body or causing cancer.

Specifically, the reactive oxygen species are produced due to various physical, chemical and environmental factors such as in vivo enzyme system, reductive metabolism, chemicals, pollutants and photochemical reactions. The produced reactive oxygen species are known to cause cellular aging and various diseases including cancer by destroying the cellular components such as lipids, proteins, saccharides and DNA. In addition, various in vivo peroxides including lipid peroxides produced by lipid peroxidation by these reactive oxygen species cause a variety of diseases by inducing functional disorders through oxidative damage to cells. Therefore, there have been many developments and studies on antioxidants that inhibit oxidation by the reactive oxygen species.

Antioxidants are widely distributed in plant and animal systems. As the antioxidants, non-enzymatic antioxidants such as glutathione (GSH), bilirubin, vitamin C, vitamin E, catechin, quercetin, flavonoids (β-carotene, lycopene, lutein, anthocyanin, resveratrol) and isoflavones (genistein, daidzein) and enzymatic antioxidants such as superoxide dismutase (SOD), peroxidase and thioredoxin (TRX) have been known.

In particular, since the reactive oxygen species are strongly associated with skin aging, there have been many attempts to achieve antioxidant and anti-aging effects to the skin by mixing antioxidants to a skin external preparation.

For example, Korean Patent Publication No. 2016-0016382 discloses that antioxidant and antibacterial activities can be obtained by adding Niaouli extract to a composition for skin external application.

Further, Korean Patent Publication No. 2015-0087146 discloses that a composition for improving the skin comprising tabersonine can be used to improve skin properties and exhibit an antioxidant effect.

These patents have some efficacy in preventing oxidation of the skin, but the effect is not sufficient. Specifically, when natural antioxidants are applied to the skin, it cannot be expected to have substantially sufficient effect. When artificial antioxidants are used, antioxidant activity is excellent, but their use is limited due to concerns about human body safety, processing stability and the like. Therefore, it is necessary to develop a composition having an excellent antioxidant effect without being harmful to the human skin.

PRIOR ART DOCUMENT

Patent Document 1

Korean Patent Publication No. 2016-0016382 (2016 Feb. 15), SKIN EXTERNAL COMPOSITION COMPRISING THE NIAOULI

Patent Document 2

Korean Patent Publication No. 2015-0087146 (2015 May 29), COMPOSITION FOR IMPROVING SKIN

DISCLOSURE

Technical Problem

Accordingly, the present inventors had been continuing research to solve the above problems. As a result, the inventors of the present invention have identified that an antioxidant composition for the skin comprising a compound that helps restore function of antioxidants together with *Saccharomyces* ferment showed better antioxidant effect.

Accordingly, an object of the present invention is to provide an antioxidant composition for the skin having an excellent antioxidant effect.

Technical Solution

According to an object of the present invention, there is provided an antioxidant composition for the skin comprising: *Saccharomyces* ferment; and at least one of α-ketoglutaric acid and niacinamide.

The *Saccharomyces* ferment may comprise thioredoxin.

The *Saccharomyces* ferment may be prepared by using yeast of *Saccharomyces* genus.

The *Saccharomyces* ferment may be included in an amount of from 0.000001 to 30% by weight based on the total weight of the antioxidant composition for the skin.

The α-ketoglutaric acid may be included in an amount of from 0.000001 to 50% by weight based on the total weight of the antioxidant composition for the skin.

The niacinamide may be included in an amount of from 0.000001 to 10% by weight based on the total weight of the antioxidant composition for the skin.

The α-ketoglutaric acid and the niacinamide may be mixed at a weight ratio of from 5000:1 to 1:5000.

Further, the present invention provides a composition for skin external application comprising the antioxidant composition for the skin.

Moreover, the present invention provides a cosmetic composition comprising the antioxidant composition for the skin.

Advantageous Effect

In the antioxidant composition for the skin according to the present invention, the antioxidants contained in the *Saccharomyces* ferment shows the antioxidant effect by eliminating reactive oxygen species and restores the activity of the antioxidants oxidized through the compounds with high reduction power. Accordingly, the antioxidant can increase persistence of the antioxidant effect of the antioxidant composition for the skin containing thereof.

Accordingly, when the composition is commercialized as a skin external preparation and cosmetics and used to the skin, it can maximize the antioxidant effect, thereby preventing skin aging caused by oxidation and improving skin condition.

BEST MODE

Hereinafter, the present invention will be described in more detail.

Herein, the term "antioxidant effect" or "antioxidant efficacy" refers to the inhibition of cellular oxidation by highly reactive free radical or reactive oxygen species due to the oxidative stress caused by intracellular metabolism or UV light, and it includes the removal of free radical or reactive oxygen species, thereby reducing cellular damage.

The present invention provides an antioxidant composition for the skin having an excellent antioxidant effect.

Reactive oxygen species are generated during normal intracellular activity and are crucial to cell growth and survival. Oxidative stress is a phenomenon that reactive oxygen species react with DNA, proteins or lipids and damages those due to an imbalance between the production of the reactive oxygen species and the antioxidant reaction removing the reactive oxygen species. It is known as a major cause of aging or various chronic diseases such as cancer, diabetes and arteriosclerosis. This oxidative stress is inevitable for living organisms that live with oxygen. But, recent harmful stimuli from the outside such as radiation, ozone, heavy metals, fine dust, UV rays, pollutants such as tobacco, inflammation caused by virus and bacterial infection cause a rapid increase in the body's oxidative stress. Accordingly, the living body has a variety of antioxidant systems based on redox response as a defense mechanism against reactive oxygen species, and thioredoxin system is one of the representative systems.

Thioredoxin (TRX) is a low-molecular-weight protein having a molecular weight of from 10,000 to 13,000, and is a coenzyme that donates hydrogen ions when a ribonucleotide reduction enzyme reduces ribonucleotides. Thioredoxin has an active site called -Cys-Gly-Pro-Cys-, which has an oxidized form that forms a disulfide (S—S) bond between two cysteine residues and a reduced form that forms a dithiol (—SH—SH), and therefore, it is an intracellular redox-controlling factor. This thioredoxin eliminates the reactive oxygen species in the cells by reducing them, but thioredoxin is oxidized at the same time. Accordingly, it cannot perform antioxidant function anymore, and it is difficult to produce in the body itself. Therefore, it is required to supply new thioredoxin.

Accordingly, in order to ensure a sustained antioxidant effect of the antioxidant composition for the skin, the present invention provides an antioxidant composition for the skin, which comprises a compound that produces NADPH (nicotinamide adenine dinucleotide phosphate hydrate) required for the reduction of antioxidants, together with *Saccharomyces* ferment having an antioxidant effect.

Specifically, the antioxidant composition for the skin according to the present invention comprises a mixture of *Saccharomyces* ferment and at least one of α-ketoglutaric acid and niacinamide.

The *Saccharomyces* ferment of the antioxidant composition for the skin according to the present invention is a product obtained by a process of adding yeast added to the raw material and then fermenting thereof, and includes thioredoxin.

The *Saccharomyces* ferment is a fermented product obtained by fermenting a raw material with yeast of *Saccharomyces* genus. It can be directly manufactured through a method conventionally performed in the art, or a commercially available product can be purchased for use. At this time, the raw material is not particularly limited, but it may be, for example, rice, sweet rice, brown rice, black rice, rice bran, barley, wheat, rye, oats, foxtail millet, sorghum, corn, buckwheat, adlay, proso millet, potato, sweet potato, cassava, yam, tapioca and the like.

In the present invention, as the *Saccharomyces* ferment, *Saccharomyces* ferment manufactured by Pharma Food International Company Ltd. may be used. The *Saccharomyces* ferment may be prepared by fermenting a mixture of unprocessed refined rice wine and yeast of *Saccharomyces* genus and then filtering the ferment thus obtained.

The yeast of *Saccharomyces* genus may be *Saccharomyces Cerevisiae*, *Saccharomyces Carlsbergensis*, *Saccharomyces pastorianus* and the like.

The thioredoxin is produced by decomposing organic matters in a raw material by yeast, and it plays an important role in reducing reactive oxygen species excessively produced by various oxidative stresses, thereby inhibiting oxidation by the reactive oxygen species. In particular, since a pair of cysteine residues present in the active site of thioredoxin is conserved from prokaryotes to eukaryotes and is a protein shared by all living organisms on the earth, even if produced in vitro, it is very harmless to the human body.

The amount of the thioredoxin may be from 0.001 g to 0.005 g, preferably from 0.0015 g to 0.003 g based on *Saccharomyces* ferment 1 g. When the amount of the is less than the above range, it may be difficult to obtain the antioxidant effect of the thioredoxin, and when the amount thereof is over the above range, there may be a problem that the economical efficiency of the final product may be deteriorated because much time and cost are required for purification.

The *Saccharomyces* ferment may be used in an amount of from 0.000001 to 30% by weight, preferably from 0.000001 to 10% by weight, based on the total weight of the antioxidant composition for the skin. When the amount of the *Saccharomyces* ferment is less than the above range, the antioxidant effect may be insignificant, and when the amount thereof is over the above range, there may be problems on safety when applying to the skin or on processing.

The antioxidant composition for the skin according to the present invention comprises α-ketoglutaric acid or niacinamide alone or a mixture thereof, together with the aforementioned *Saccharomyces* ferment. The α-ketoglutaric acid or niacinamide acts as a source of NADPH to reduce thioredoxin oxidized by the body's antioxidant activity.

The α-ketoglutaric acid is an intermediate metabolite of the TCA cycle, an energy metabolism in the body, and it inhibits ATP synthase during the production of adenosine triphosphate (ATP), thereby reducing the consumption of the intermediate NAD (nicotinamide adenine dinucleotide). Thus, the remaining NAD forms NADPH having reducing power to enable the reuse of thioredoxin.

The α-ketoglutaric acid can be synthesized directly or a commercially available product can be used, but not limited thereto.

The α-ketoglutaric acid may be used in an amount of from 0.000001 to 50% by weight, preferably from 0.00001 to 30% by weight, based on the total weight of the antioxidant composition for the skin. When the amount of the α-ketoglutaric acid is less than the above range, the effect may be insignificant, and when the amount is over the above range, it may cause adverse effects on the human body and it may be difficult to uniformly dissolve it, so that blending in the formulation may be impossible.

The niacinamide is a physiologically active amide of vitamin B3, also known as nicotinamide or pyridine-3-carboxylic acid. It not only has an antioxidant effect but also acts as a precursor of NADPH, which is converted into NADPH in the body to help reduction of thioredoxin.

The niacinamide can be synthesized directly or a commercially available product can be used, but not limited thereto.

The niacinamide may be used in an amount of from 0.000001 to 10% by weight, preferably from 0.000001 to 5% by weight, based on the total weight of the antioxidant composition for the skin. When the amount thereof is less than the above range, the effect obtained by using the niacinamide cannot be obtained, and when the amount thereof is over the above range, it may be highly likely to cause irritation to the skin and may have a great influence on the stability of the formulation.

As mentioned above, the α-ketoglutaric acid and the niacinamide may be used alone or in a mixture thereof, and the mixture of the α-ketoglutaric acid and the niacinamide may be mixed at weight ratio of from 5000:1 to 1:5000, preferably from 1000:1 to 1:1000, more preferably from 200:1 to 1:200, and most preferably from 50:1 to 1:50. When the weight ratio is out of the above weight ratio, there may be adverse effects or lack of improvement.

The antioxidant composition for the skin containing the above-mentioned composition not only has an excellent antioxidant effect when applied to the skin but also maintains its effect continuously, thereby preventing skin aging caused by oxidation and improving skin properties.

The antioxidant composition for the skin of the present invention may comprise ingredients commonly used in addition to the above ingredients. For example, it may comprise oil and fat components, moisturizer, softener, surfactant, organic and inorganic pigments, organic powder, ultraviolet absorber, preservative, anti-forming agent, thickener, bactericide, antioxidant, plant extracts, pH adjusting agent, alcohol, colorant, fragrance, blood circulation accelerator, coolant, antiperspirant and the like.

Further, the present invention provides a composition for skin external application comprising the antioxidant composition for the skin.

When the antioxidant composition for the skin is used as a composition for skin external application, the composition may be formulated with a dermatologically acceptable carrier, medium or base. In addition, the composition may comprise additives which are generally used in the dermatological field, for example, fatty substance, organic solvent, solubilizing agent, thickener, gelling agent, softener, antioxidant, suspending agent, stabilizer, foaming agent, fragrance, surfactant, water, ionic or non-ionic emulsifying agent, filler, chelating agent, preservative, vitamins, blocking agent, wetting agent, essential oil, dye, pigment, hydrophilic or hydrophobic activator, lipid vesicle, or other components which are generally used in a composition for skin external application. These additives are comprised in amounts which are generally used in the dermatological field.

The composition for skin external application is not limited thereto, but it may be provided as a formulation selected from the group consisting of an ointment, a paste, a lotion, a cream, a gel, a solution, a suspension, an emulsion, a patch or a spray.

In the composition for skin external application, the effective amount of the antioxidant composition for the skin according to the present invention may vary depending on the constitution of composition for skin external application, the formulation type, the age, body weight, health condition and sex of a user, administration time, administration route, administration method and the like. For example, the antioxidant composition for the skin of the present invention may be comprised in an amount of from 0.0001 to 10% by weight, preferably from 0.0001 to 1% by weight, based on the total weight of the composition for skin external application. When the amount of the antioxidant composition for the skin of the present invention is less than 0.0001 wt %, it may be difficult to obtained sufficient antioxidant effect, and when the amount thereof is over 10 wt %, there may be adverse effects such as itching, rash and allergies.

Further, the present invention provides a cosmetic composition comprising the antioxidant composition for the skin.

When using the antioxidant composition for the skin as a cosmetic composition, the composition may be formulated with a cosmetically acceptable carrier, medium or base. In addition, the composition may comprise additives which are generally used in the cosmetic field, for example, fatty substance, organic solvent, solubilizing agent, thickener, gelling agent, softener, antioxidant, suspending agent, stabilizer, foaming agent, fragrance, surfactant, water, ionic or non-ionic emulsifying agent, filler, chelating agent, preservative, vitamins, blocking agent, wetting agent, essential oil, dye, pigment, hydrophilic or hydrophobic activator, lipid vesicle, or other components which are generally used in cosmetics. These additives are comprised in amounts which are generally used in the cosmetic field.

The cosmetic composition may be generally formulated as an emulsified formulation and a solubilized formulation. Cosmetics as the emulsified formulation include nourishing toner, cream, essence and the like, and cosmetics as the solubilized formulation include softening toner. Specifically, the cosmetic composition is not limited thereto, but it may have formulation selected from the group consisting of ointment, lotion, cream, gel, solution, suspension, emulsion, patch and spray. More specifically, it may be provided as a formulation, for example, as a skin care product such as softening toner, nourishing toner, lotion, essence, cream, gel, pack, patch, mask and mist, a makeup product such as a makeup base, foundation, powder, mascara and lipstick, a makeup remover product such as cleansing oil, cleansing cream, cleansing lotion, cleansing water and point makeup remover, or a cleansing product such as soap, cleansing foam and body wash.

When the antioxidant composition is commercialized as a cosmetic product, the a wash-off type cosmetic such as make-up remover or cleanser in which an effective ingredient remains on the skin in a short period of time may comprise the antioxidant composition in a relatively high concentration. On the other hand, a leave-on type cosmetic such as toner, lotion, cream, and essence in which the active ingredient remains on the skin for a long period of time may comprise the antioxidant composition in a lower concentration than the wash-off type cosmetic. For example, the antioxidant composition for the skin may be comprised in an amount of from 0.0001 to 10% by weight, preferably from 0.0001 to 1% by weight, based on the total weight of the cosmetic composition. When the amount of the antioxidant composition for the skin of the present invention is less than 0.0001 wt %, it may be difficult to obtain sufficient antioxidant effect, and when the amount thereof is over 10 wt %, there may be adverse effects such as itching, rash and allergies.

When the formulation of the present invention is ointment, paste, cream or gel, animal oil, vegetable oil, wax, paraffin, starch, tragacanth, cellulose derivatives, polyethylene glycol, silicone, bentonite, silica, talc or zinc oxide may be used as a carrier component.

When the formulation of the present invention is powder or spray, lactose, talc, silica, aluminum hydroxide, calcium silicate or polyamide powder may be used as a carrier component. In particular, when the formulation is spray, it may further include propellant such as chlorofluorohydrocarbon, propane/butane or dimethyl ether.

When the formulation of the present invention is solution or emulsion, solvent, solubilizer or emulsifier may be used as a carrier component. For example, water, ethanol, isopropanol, ethyl carbonate, ethyl acetate, glycerin, carbomer, benzyl alcohol, benzyl benzoate, propylene glycol, 1,3-butylene glycol oil, glycerol aliphatic ester, caprylic/capric triglyceride, hydrogenated polydecene, cetearyl glucoside, sorbitan stearate, polyethylene glycol or cetearyl alcohol may be used.

When the formulation of the present invention is suspension, liquid diluent such as water, ethanol or propylene glycol, suspending agent such as ethoxylated isostearyl alcohol, polyoxyethylene sorbitol ester and polyoxyethylene sorbitan ester, microcrystalline cellulose, aluminum metahydroxide, bentonite, agar or tragacanth may be used as a carrier component.

When the formulation of the present invention is cleanser, it may be classified into surfactant-containing cleanser formulation and surfactant-free cleanser formulation, and it can be wiped off or removed or rinsed with water after applied to the skin. When the formulation is surfactant-containing cleanser, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamidobetain, aliphatic alcohol, fatty acid glyceride, fatty acid diethanolamide, vegetable oil, lanolin derivatives, or ethoxylated glycerol fatty acid ester and the like may be used as a carrier. Further, the surfactant-containing cleanser formulation may be cleansing foam, cleansing water, cleansing towel and cleansing pack, and the surfactant-free cleanser formulation may be cleansing cream, cleansing lotion, cleansing water and cleansing gel, but not limited thereto.

When the formulation of the present invention is soap or body wash, it can be wiped off or removed or rinsed with water after applied to the skin. Specifically, the soap may be liquid soap, powder soap, solid soap and oil soap.

MODE FOR INVENTION

Hereinafter, the preferred embodiment of the present invention will be described in detail based on examples. However, the embodiments of the present invention may be modified in various ways, and the scope of the present invention should not be interpreted as being limited to the examples. The embodiments of the present invention are provided just for explaining the present invention more perfectly to those having ordinary skill in the art.

Test Example 1

Evaluation of Expression of Antioxidant Enzyme-related Gene

In order to investigate the effect of SOD2 and NRF2, which are enzymes involved in intracellular antioxidation, on gene expression, mRNA expression level was quantified by RT-PCR.

The SOD2 (superoxide dismutase 2) is a kind of antioxidant enzyme produced in the human body. It converts superoxide anion ($O2^{-*}$), which is reactive oxygen species, into hydrogen peroxide through dismutation reaction, and finally decomposes the hydrogen peroxide into water and oxygen to eliminate the reactive oxygen species. Further, the NRF2 (nuclear factor erythroid 2-related factor 2) binds to the ARE (antioxidant response element) located on the genes of the antioxidant enzyme and the detoxifying enzyme when oxidative stress is applied to promote the activity of the antioxidant defense system in the cell. The gene expression levels of these two enzymes were used to evaluate the intracellular antioxidant effect.

The cells used in this Test Example 1 were keratinocytes (NHK), and normal human keratinocytes (Human epidermal neonatal keratinocyte cells) purchased from Lonza, Inc. (Walkersville, Md., USA) were serially cultured and then cultured in a $CO_2$ incubator under conditions of 37° C., 5% $CO_2$. The cell culture was followed by the guidelines of Lonza, Inc. (Walkersville, Md., USA). KGM-Gold SingleQuot kit was added to 500 ml KBM-Gold medium.

*Saccharomyces* ferment, α-ketoglutaric acid and niacinamide were added to the keratinocyte culture at the concentrations shown in the following Table 1 and cultured for 24 hrs. After removing the culture, total RNA in the cells was isolated by using Trizol reagent (Invitrogen, Carlsbad, Calif., USA). The isolated RNA was purified once more using a RNA kit of Quiagen (Qiagen RNeasy kit, Qiagen, Valencia, Calif.), and then subjected to Agilent 2100 BioAnalyzer (Agilent Technologies, Santa Clara, Calif., USA) to confirm the quality of RNA. cDNA was synthesized form the isolated RNA using a reverse transcription kit of Invitrogen (Superscript Reverse Transcriptase (RT) II kit, Invitrogen, Carlsbad, Calif.), and amplified with PCR reaction solution using Taqman probe (SOD2, NRF2, RPLPO) by real time-reverse transcription polymerase chain reaction (Q-RT-PCR).

The final PCR product was electrophoresed on 1.0% agarose gel, stained with Cyber Green and then quantified under 320 nm UV. The above procedure was performed to determine the expression rate of the genes related to the antioxidant enzymes and the results are shown in the following Table 2.

TABLE 1

|  | *Saccharomyces* ferment (ppm) | α-Ketoglutaric acid (ppm) | Niacinamide (ppm) |
| --- | --- | --- | --- |
| Control | — | — | — |
| Comparative Example 1 | 100 | — | — |
| Example 1 | 50 | 50 | — |
| Example 2 | 50 | — | 50 |
| Example 3 | 50 | 25 | 25 |

TABLE 2

|  | SOD2 (Relative mRNA Level) | NRF2 (Relative mRNA Level) |
| --- | --- | --- |
| Control | 1.00 | 1.00 |
| Comparative Example 1 | 1.19 | 1.24 |
| Example 1 | 1.37 | 1.43 |
| Example 2 | 1.32 | 1.32 |
| Example 3 | 1.54 | 1.59 |

As shown in Table 2, in the case of Example according to the present invention, it was confirmed that the expression of the antioxidant enzyme gene was significantly increased compared with Comparative Example 1, which was treated with only *Saccharomyces* ferment, and control without any treatment. Further, Example 3, which was treated with both of α-ketoglutaric acid and niacinamide, showed higher expression rate than Examples 1 and 2, which were treated with α-ketoglutaric acid or niacinamide alone. Accordingly, the synergistic effect by using both α-ketoglutaric acid and niacinamide was confirmed.

Formulation Example 1

Preparation of Skin External Preparation

1. Ointment

According to the composition shown in Table 3 below, ointment containing the antioxidant composition for the skin of the present invention was prepared according to the conventional method.

TABLE 3

| Ingredient | Ointment (Unit: wt %) |
| --- | --- |
| *Saccharomyces* ferment | 1.0 |
| α-Ketoglutaric acid | 1.0 |
| Niacinamide | 1.0 |
| Beta-1,3-glucan | 10.0 |
| Wax | 10.0 |
| Polysorbate | 5.0 |
| PEG 60 hydrogenated castor oil | 2.0 |
| Sorbitan sesquioleate | 0.5 |
| Vaseline | 5.0 |
| Liquid paraffin | 10.0 |
| Squalene | 5.0 |
| Shea butter | 3.0 |
| Caprylic/Capric triglyceride | 5.0 |
| Glycerin | 10.0 |
| Propylene glycol | 10.2 |
| Triethanolamine | 0.2 |

TABLE 3-continued

| Ingredient | Ointment (Unit: wt %) |
| --- | --- |
| Preservative, Fragrance | 0.1 |
| Purified water | To 100 |

2. Gel

According to the composition shown in Table 4 below, gel containing the antioxidant composition for the skin of the present invention was prepared according to the conventional method.

TABLE 4

| Ingredient | Gel (Unit: wt %) |
| --- | --- |
| *Saccharomyces* ferment | 1.0 |
| α-Ketoglutaric acid | 1.0 |
| Niacinamide | 1.0 |
| Beta-1,3-glucan | 0.1 |
| Ethylene diamine tetraacetic acid | 0.05 |
| Glycerin | 5.0 |
| Carboxyvinyl polymer | 0.3 |
| Ethanol | 5.0 |
| PEG 60 hydrogenated castor oil | 0.5 |
| Trierthanolamine | 0.3 |
| Preservative, Fragrance | 0.1 |
| Purified water | To 100 |

Formulation Example 2

Preparation of Cosmetics

1. Nourishing Cream

According to the composition shown in Table 5 below, nourishing cream containing the antioxidant composition for the skin of the present invention was prepared according to the conventional method.

TABLE 5

| Ingredient | Nourishing cream (Unit: wt %) |
| --- | --- |
| *Saccharomyces* ferment | 1.0 |
| α-Ketoglutaric acid | 1.0 |
| Niacinamide | 1.0 |
| Vegetable hydrogenated oil | 1.5 |
| Stearic acid | 0.6 |
| Glycerol stearate | 1.0 |
| Stearyl alcohol | 2.0 |
| Polyglyceryl-10 pentastearate & behenyl alcohol & sodium stearoyl lactylate | 1.0 |
| Arachidyl behenyl alcohol & arachidyl glucoside | 1.0 |
| Cety aryl alcohol & cetearyl glucoside | 2.0 |
| PEG-100 stearate & glycerol oleate & propylene glycol | 1.5 |
| Caprylic/Capric triglyceride | 11.0 |
| Cyclomethicone | 6.0 |
| Preservative, Fragrance | 0.1 |
| Triethanlamine | 0.1 |
| Purified water | To 100 |

2. Nourishing Toner

According to the composition shown in Table 6 below, nourishing toner containing the antioxidant composition for the skin of the present invention was prepared according to the conventional method.

TABLE 6

| Ingredient | Nourishing toner (Unit: wt %) |
|---|---|
| *Saccharomyces* ferment | 1.0 |
| α-Ketoglutaric acid | 1.0 |
| Niacinamide | 1.0 |
| Beta-1,3-glucan | 1.0 |
| Wax | 4.0 |
| Polysorbate | 1.5 |
| Sorbitan sesquioleate | 1.5 |
| Liquid paraffin | 0.5 |
| Caprylic/Capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, Fragrance | 0.1 |
| Purified water | To 100 |

INDUSTRIAL AVAILABILITY

The antioxidant composition for the skin of the present invention exhibits an excellent antioxidant effect and enables the manufacture of various products such as cosmetics and medicines.

The invention claimed is:

1. An antioxidant composition for the skin comprising: *Saccharomyces* ferment,
α-ketoglutaric acid and
niacinamide,
wherein the α-ketoglutaric acid is included in an amount of from 0.00001 to 30% by weight based on the total weight of the antioxidant composition for the skin,
wherein the niacinamide is included in an amount of from 0.000001 to 5% by weight based on the total weight of the antioxidant composition for the skin, and
wherein the α-ketoglutaric acid and the niacinamide is mixed at a weight ratio of 1:1.

2. The antioxidant composition for the skin of claim 1, wherein the *Saccharomyces* ferment comprises thioredoxin.

3. The antioxidant composition for the skin of claim 1, wherein the *Saccharomyces* ferment is included in an amount of from 0.000001 to 30% by weight based on the total weight of the antioxidant composition for the skin.

4. The antioxidant composition for the skin of claim 1, wherein the antioxidant composition for the skin is in the form of a formulation selected from the group consisting of ointment, paste, lotion, cream, gel, solution, suspension, emulsion, patch and spray.

* * * * *